United States Patent [19]

Morita et al.

[11] Patent Number: 5,567,388
[45] Date of Patent: Oct. 22, 1996

[54] APPARATUS FOR MEASURING TOTAL ORGANIC CARBON

[75] Inventors: Youzo Morita, Kameoka; Keiji Inoue, Suita, both of Japan

[73] Assignee: Shimadzu Corporation, Japan

[21] Appl. No.: 525,070

[22] Filed: Sep. 8, 1995

Related U.S. Application Data

[63] Continuation of Ser. No. 915,578, Jul. 20, 1992, abandoned.

[30] Foreign Application Priority Data

Jul. 29, 1991 [JP] Japan ................... 3-212942

[51] Int. Cl.[6] ................................. G01N 31/12
[52] U.S. Cl. ................... 422/80; 422/68.1; 422/78; 436/146; 210/321.75; 210/321.78; 210/639; 210/644
[58] Field of Search ................... 422/78, 79, 80, 422/68.1; 436/145, 146; 210/321.75, 639, 644, 321.78

[56] References Cited

U.S. PATENT DOCUMENTS

| | | | |
|---|---|---|---|
| 3,401,798 | 9/1968 | Nyrop | 210/321.75 |
| 3,607,071 | 9/1971 | Staffin et al. | 436/146 |
| 3,955,924 | 5/1976 | Northmore et al. | 436/146 |
| 3,958,941 | 5/1976 | Regan | 422/78 |
| 3,958,945 | 5/1976 | Takahashi | 422/78 |
| 4,066,402 | 1/1978 | Komiyama et al. | 422/78 |
| 4,293,522 | 10/1981 | Winkler | 422/78 |
| 4,769,217 | 9/1988 | Sienkiewicz | 436/146 X |
| 4,968,485 | 11/1990 | Morita | 422/78 X |
| 5,039,416 | 8/1991 | Loew et al. | 210/639 X |
| 5,085,772 | 2/1992 | Busch-Sorensen | 210/321.75 X |
| 5,094,817 | 3/1992 | Aoki et al. | 422/68.1 |
| 5,132,094 | 7/1992 | Godec et al. | 422/78 X |
| 5,271,900 | 12/1993 | Morita | 436/145 X |
| 5,412,763 | 5/1995 | Jeffers | 436/146 X |
| 5,425,919 | 7/1995 | Inoue et al. | 422/78 X |

*Primary Examiner*—Esther Kepplinger
*Assistant Examiner*—Milton I. Cano
*Attorney, Agent, or Firm*—Klima & Hopkins, P.C.

[57] ABSTRACT

An inorganic carbon removing part defined by has a double tube structure formed by an inner tube of polytetrafluoroethylene having continuous pores and an outer tube of resin. An acidified sample solution is guided into the inner tube and an alkalified sample solution is guided into the outer tube, and inorganic carbon contained in the acidified sample solution is outwardly moved toward the alkalified sample solution to be removed. The acidified sample solution, from which inorganic carbon is removed, is injected into a combustion tube, so that a carbon component contained in the sample solution is converted into carbon dioxide and detected by a detecting part. Since the alkalified sample solution contains purgeable organic carbon components of the same concentration as the acidified sample solution, the content of total organic carbon is correctly measured with no loss of the purgeable organic carbon components.

7 Claims, 4 Drawing Sheets

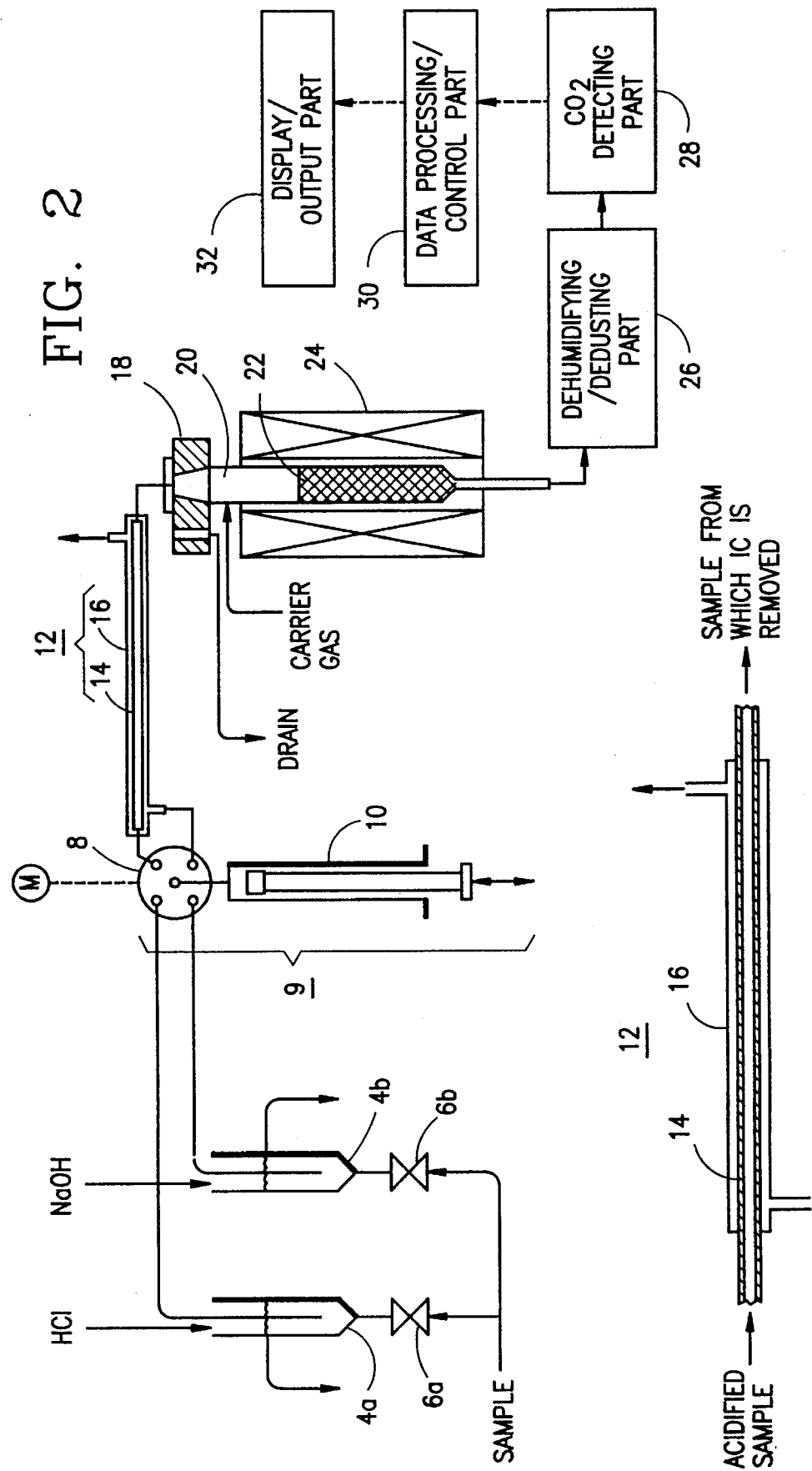

APPARATUS FOR MEASURING TOTAL ORGANIC CARBON

This application is a continuation of application Ser. No. 07/915,578, filed Jul. 20, 1992 now abandoned.

BACKGROUND OF THE INVENTION

1. Field of the Invention

The present invention relates to an apparatus for, and a method of measuring total organic carbon (TOC) which is contained in sample water.

2. Description of the Background Art

In general, the content of total organic carbon which is contained in sample water is obtained by a method of independently measuring the contents of total carbon (TC) and inorganic carbon (IC) contained therein and calculating the difference therebetween as follows:

$$TOC=TC-IC$$

In this method, however, measurement errors caused in the measurement of the content of total carbon and the measurement of the content of inorganic carbon are included in the resulting TOC content, to problematically increase the total measurement error.

Another method of measuring the content of total organic carbon is called acid sparging treatment (or pretreatment). This method comprises the steps of acidifying sample water by adding inorganic acid thereto, sparging the acidified sample water with a gas containing no carbonic acid gas for removing inorganic carbon, and thereafter converting carbon, i.e., total organic carbon, which is exclusively left in the sample water, into carbonic acid gas and detecting the same, thereby measuring the content of total organic carbon. The acid sparging treatment is effectively applied to sample water which contains a considerably larger amount of inorganic carbon as compared with total organic carbon, such as that containing 100 p.p.m. of inorganic carbon and 10 p.p.m. of total organic carbon, for example, with a smaller measurement error as compared with the method of independently measuring the contents of total carbon and inorganic carbon.

With respect to still another method of measuring the content of total organic carbon, there has been proposed an apparatus for a method of introducing an acidified sample solution into a capillary which is made of a carbonic acid gas permeable material and decompressing the outer side thereof or introducing a carbonic acid gas absorbent solution such as a calcium hydroxide solution to the outer side thereof for outwardly removing inorganic carbon from the acidified sample solution through the carbonic acid gas permeable material, and thereafter measuring the content of carbon contained in the sample solution (refer to Japanese Patent Laying-Open Gazette No. 60-127460 (1985)).

In the acid sparging treatment, purgeable organic carbon (POC) which is contained in the sample is lost by volatilization during the sparging process for the acidified sample solution. If the sample contains chloroform, for example, about 100% thereof is lost. While purgeable organic carbon components include volatile and non-volatile materials, those having low boiling points and small water solubility, i.e., small affinity with water, are easily lost in general.

In the method of removing inorganic carbon contained in the acidified sample solution with the carbonic acid gas permeable material according to the aforementioned literature, a purge able organic carbon component which is contained in the sample solution is also lost through the carbonic acid gas permeable material since the decompressed gaseous phase which comes into contact with the acidified sample solution through the carbonic acid gas permeable material or the carbonic acid gas absorbent solution such as a calcium hydroxide solution contains no purgeable organic carbon component. In this case, the type of the lost purgeable organic carbon component and the degree of loss thereof are varied with the type and condition of the carbonic acid gas permeable material as employed, while a considerable amount of the purgeable organic carbon component is lost through a film of silicone rubber or polytetrafluoroethylene having continuous pores, which is employed in general.

SUMMARY OF THE INVENTION

An object of the present invention is to provide an apparatus, for and a method of measuring total organic carbon, which are adapted to remove inorganic carbon from an acidified sample solution through a carbonic acid gas permeable material while preventing loss of purgeable organic carbon components.

A total organic carbon measuring apparatus according to the present invention comprises an inorganic carbon removing part which is provided with an acidified sample solution of not more than pH 4 and an alkalified sample solution of at least pH 9 arranged on both sides of a carbonic acid gas permeable material for moving inorganic carbon contained in the acidified sample solution toward the alkalified sample solution through the carbonic acid permeable material, and a detecting part for detecting total organic carbon contained in the acidified sample solution from which inorganic carbon is removed in the inorganic carbon removing part.

The carbonic acid gas permeable material employed in the inorganic carbon removing part can be prepared from a polytetrafluoroethylene film, a silicone rubber film, a cellulose acetate film or a polyethylene film having continuous pores, or a composite film thereof. The acidified sample solution is adjusted to be not more than pH 4, preferably not more than pH 3, with addition of inorganic acid such as hydrochloric acid, nitric acid or phosphoric acid. The alkalified sample solution is adjusted to be at least pH 9, preferably at least pH 10, with addition of alkali such as sodium hydroxide or calcium hydroxide.

When an acidified sample solution and an alkalilied sample solution are arranged on both sides of a carbonic acid gas permeable material 2 as shown in FIG. 1, inorganic acid components contained in the acidified sample solution form $CO_2$, which in turn is moved toward the alkalified sample solution through the carbonic acid gas permeable material 2 and forms hydrogen carbonate ions or carbonate ions in the alkalified sample solution to be removed. On the other hand, purgeable organic carbon components such as chloroform cause no such movement since those have the same concentrations on both sides of the acidified and alkalilied sample solutions. Therefore, purgeable organic carbon components are not lost from the acidified sample solution.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 2 is a schematic diagram showing a first embodiment of the present invention;

FIG. 3 is a schematic sectional view showing an inorganic carbon removing part in the embodiment shown in FIG. 2;

DESCRIPTION OF THE PREFERRED EMBODIMENTS

Figure 1:
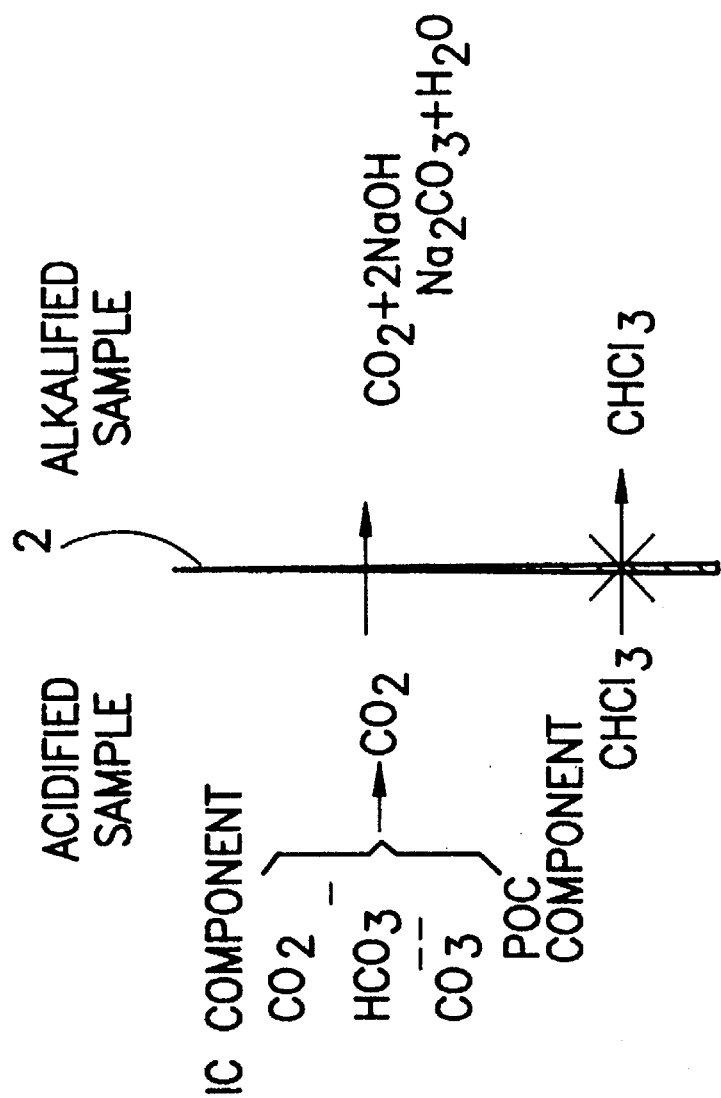
FIG. 1 illustrates the principle of the present invention.

FIG. 2 shows an apparatus according to an embodiment of the present invention.

In order to prepare an acidified sample solution and an alkalified sample solution, overflow sample containers 4a and 4b are arranged to be supplied with sample solution from bottom portions thereof through switching valves 6a and 6b, respectively. Hydrochloric acid is added to the sample container 4a, while an NaOH solution is added to the sample container 4b. The acidified sample solution and the alkalified sample solution thus prepared in the sample containers 4a and 4b, respectively, are guided to an inorganic carbon removing part 12 by a sample injector 9 including a fourway valve 8, which is driven by a motor M, and a microsyringe 10.

As shown in FIG. 3, the inorganic carbon removing part 12 has a double-tube structure which is formed by an inner tube 14 of a carbonic acid gas permeable material and an outer tube 16 of resin. While the materials for the inorganic carbon removing part 12 are not restricted, the inner tube 14 of a carbonic acid gas permeable material is prepared from a polytetrafluoroethylene tube having continuous pores, which is about 1.0 mm in inner diameter and about 0.4 mm in thickness with the maximum pore diameter of about 3.5 μm and porosity of about 70%, while the outer tube 16 is prepared from a polytetrafluoroethylene tube of about 2.4 mm in inner diameter and about 3.2 mm in outer diameter, for example. The acidified sample solution and the alkalified sample solution come into contact with each other through the polytetrafluoroethylene film of the inner tube 14 along a length of about 550 mm. The acidified sample solution is guided into the inner tube 14, while the alkalified sample solution is guided into the outer tube 16.

Referring again to FIG. 2, the acidified sample solution is guided into the inner tube 14 of the inorganic carbon removing part 12 by the sample injector 9 and the alkalilied sample solution is guided into a portion between the inner tube 14 and the outer tubes 16 of the inorganic carbon removing part 12, and the acidified sample solution flowing out from an outlet of the inner tube 14 is guided to a combustion tube 20 through a sliding sample filler hole 18 or discharged into a drain. In order to vaporize the acidified sample solution and convert total carbon components into carbon dioxide by oxidation, the combustion tube 20 is filled up with an oxidation catalyst 22 and enclosed by a heating furnace 24. The alkalified sample solution guided toward the outer tube 16 of the inorganic carbon removing part 12 is discharged to the drain.

A sample gas generated in the combustion tube 20 is guided to a $CO_2$ detecting part 28 through a dehumidifying/dedusting part 26, to be subjected to measurement of carbon dioxide. The apparatus further includes a data processing/control part 30, and a display/output part 32.

The operation of the embodiment shown in FIG. 2 is now described.

After the sample solution is introduced into the sample containers 4a and 4b through the switching valves 6a and 6b, respectively, a proper amount of hydrochloric acid is dripped in the sample container 4a for adjusting the acidified sample solution to not more than pH 4, preferably not more than pH 3, while a sodium hydroxide solution is dripped in the sample container 4b for adjusting the alkalified sample solution to at least pH 9, preferably at least pH 10. The sample solutions are stirred in the sample containers 4a and 4b, if necessary. The acidified sample solution is guided into the inner tube 14 of the inorganic carbon removing part 12 through the sample injector 9 while the alkalified sample solution is guided into the outer tube 16, and left there for a prescribed period of 2 minutes, for example. During this period, inorganic carbon contained in the acidified sample solution is moved toward the alkalified sample solution through the polytetrafluoroethylene film forming the inner tube 14, to be removed.

After a lapse of the prescribed period, the sample injector 9 supplies a prescribed amount of the acidified sample solution into the inner tube 14, so that the same amount of the acidified sample solution contained in the inner tube 14, from which inorganic carbon has been removed, is injected into the combustion tube 20. Then the sample solution is vaporized in the combustion tube 20 so that total carbon contained therein is converted into carbon dioxide, which in turn is guided through the dehumidifying/dedusting part 26 into the $CO_2$ detecting part 28, to be detected.

Thereafter a new sample is introduced into the sample containers 4a and 4b, acidified and alkalified, respectively, and fed into the inorganic carbon removing part 12 for next measurement.

Figure 4:
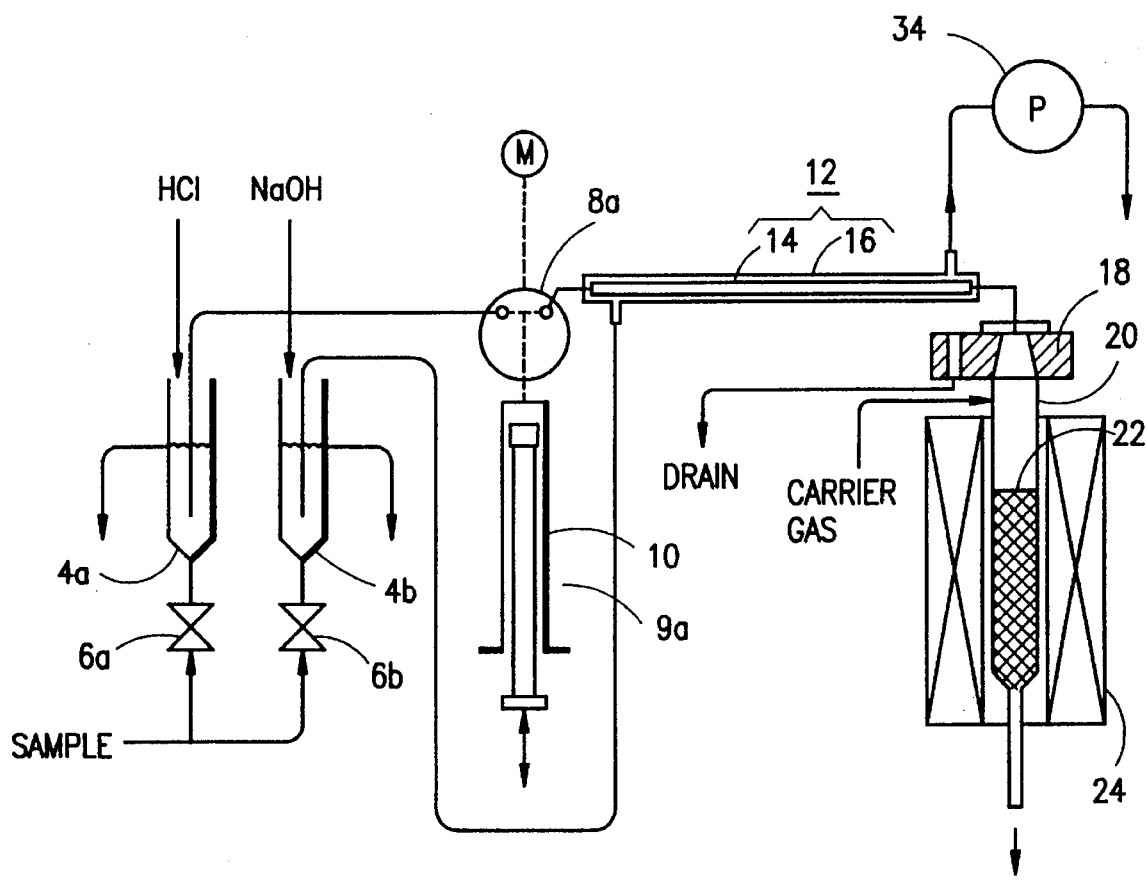
FIG. 4 is a schematic diagram showing a second embodiment of the present invention.

FIG. 4 shows an apparatus according to a second embodiment of the present invention.

The embodiment shown in FIG. 4 is different from that shown in FIG. 2 in that a sample injector 9a is formed by a three-way valve 8a and a microsyringe 10 for guiding only the acidified sample solution to the inorganic carbon removing part 12, while the alkalified sample solution is directly guided to an outer tube of the inorganic carbon removing part 12 to be continuously discharged by a pump 34.

Also in the apparatus shown in FIG. 4, the acidified sample solution is left in an inner tube of the inorganic carbon removing part 12 for removal of inorganic carbon, and then guided to a combustion tube 20 for measurement of total organic carbon through an operation similar to that shown in FIG. 2.

Figure 5:
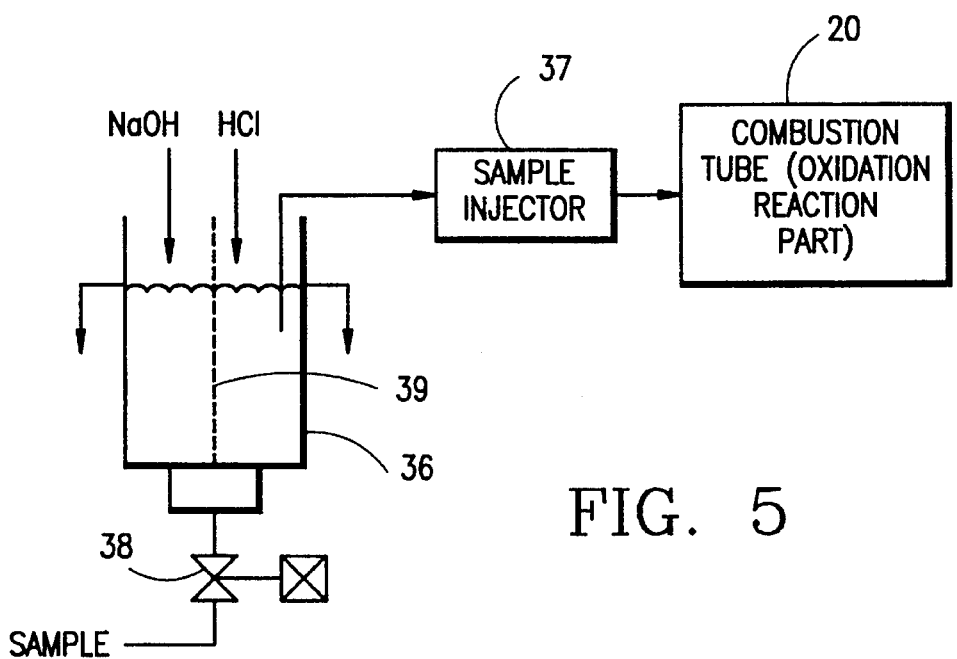
FIG. 5 is a schematic diagram showing a third embodiment of the present invention.

FIG. 5 shows an apparatus according to a third embodiment of the present invention.

In the embodiment shown in FIG. 5, inorganic carbon is removed in an overflow sample container 36. The interior of the sample container 36 is divided into two regions by a carbonic acid gas permeable material film 39 which is provided at its center, so that the sample solution is supplied to each region from the bottom portion of the sample container 36 through a switching valve 38. The carbonic acid gas permeable material film 39 is prepared from a polytetrafluoroethylene film having continuous pores, for example. In the sample container 36, inorganic acid such as hydrochloric acid is added to the sample solution contained in one region to acidify the same, while an alkali solution such as an NaOH solution is added on the sample solution contained in the other region to alkalify the same. The acidified sample solution and the alkalified sample solution are left in the sample container 36 for a prescribed period so that inorganic carbon is removed from the acidified sample solution, which in turn is guided to a combustion tube 20 through a sample injector 37 and converted into carbon dioxide for measurement of total carbon.

Figure 6:
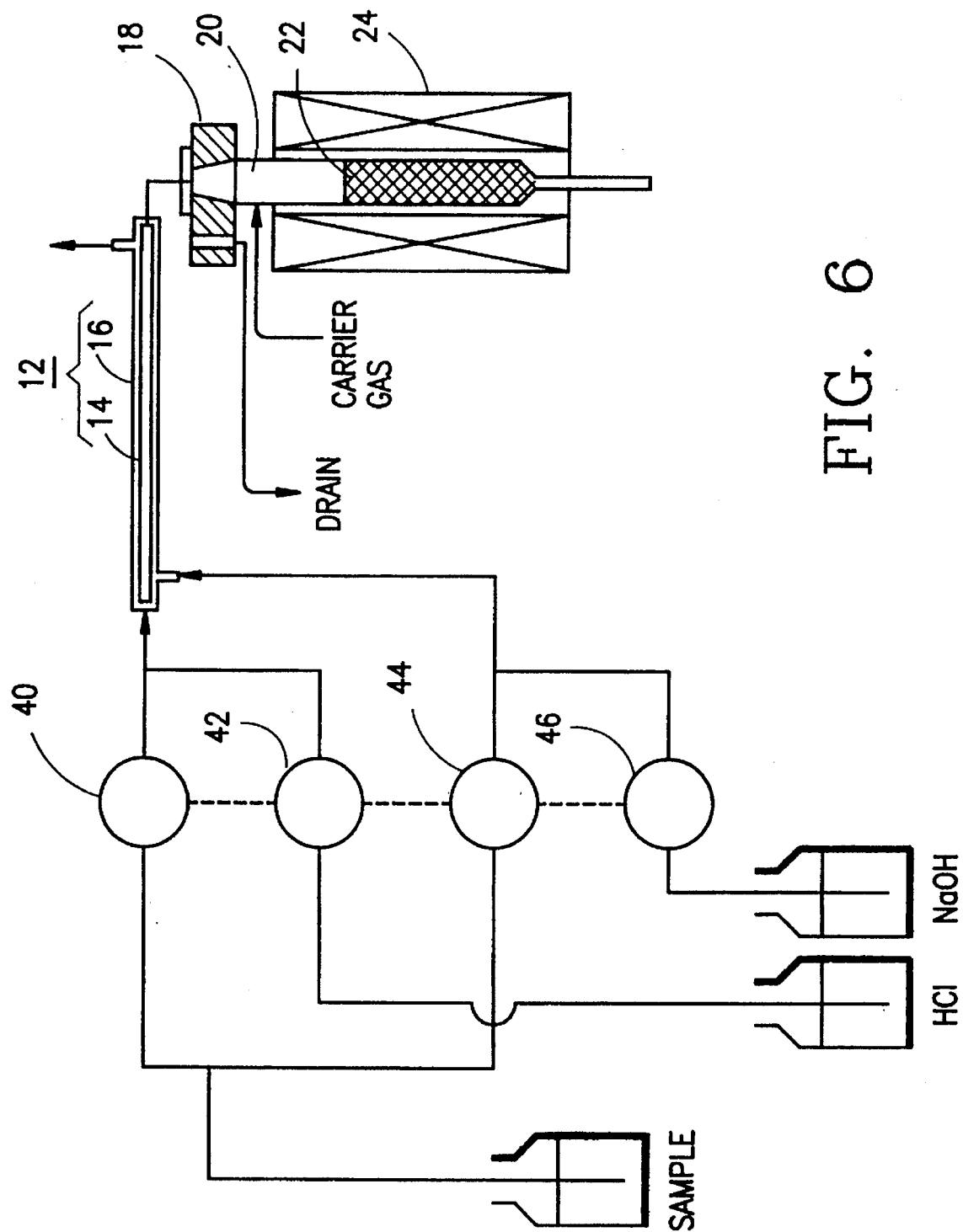
FIG. 6 is a schematic diagram showing a fourth embodiment of the present invention.

FIG. 6 shows an apparatus according to a fourth embodiment of the present invention.

While the overflow sample containers are employed in the embodiment shown in FIG. 2 for acidifying and alkalifying the sample solutions, a sample solution is mixed with hydrochloric acid and an alkali solution in different passages to be acidified and alkalified, respectively, in the embodiment shown in FIG. 6. To this end, the sample solution is guided into an inner tube of an inorganic carbon removing part 12 by a pump 40 while hydrochloric acid is guided by a pump 42 to be mixed with the sample solution. The sample solution is also guided into an outer tube of the inorganic carbon removing part 12 by a pump 44 while an NaOH solution is guided by a pump 46 to be mixed with the sample solution. The pumps 40, 42, 44 and 46 can be formed by peristaltic pumps which are driven by a single driving part in common. The acidified sample solution passed through the inorganic carbon removing part 12 is guided to a combustion tube 20 similarly to the embodiment shown in FIG. 2, so that total carbon components are converted into carbon dioxide and detected.

In each of the embodiments shown in FIGS. 2 and 4, it is possible to use a single overflow sample container to add acid (or alkali) to a sample solution which is first introduced thereinto for acidifying (or alkalifying) the same and introduce the sample into the inner tube (or the outer tube) of the inorganic carbon removing part, and then change the sample solution in the container and add alkali (or acid) for alkalifying (or acidifying) the same, introduce the sample solution into the outer tube (or the inner tube) of the inorganic carbon removing part for removing inorganic carbon from the acidified sample solution contained in the inner tube (or the outer tube).

In each of the embodiments shown in FIGS. 2 and 4, further, it is also possible to introduce alkalified and acidified sample solutions into the inner tube 14 and the outer tube 16 of the inorganic carbon removing part 12, respectively, to guide the acidified sample solution from the outer tube 16 to the combustion tube 20 for measurement of total organic carbon.

The combustion tube 20 for converting the carbon component contained in the sample solution into carbon dioxide can be replaced by another oxidation reaction part.

According to the present invention, acidified and alkalified sample solutions are arranged on both sides of a carbonic acid gas permeable material film in an inorganic carbon removing part so that inorganic carbon contained in the acidified sample solution is moved toward the alkalified sample solution to be removed, whereby it is possible to effectively remove inorganic carbon in the inorganic carbon removing part while suppressing loss of purgeable organic carbon components. In the second embodiment employing a polytetrafluoroethylene film having continuous pores as the carbonic acid gas permeable material, inorganic carbon can be reduced to about 0.5 p.p.m. in a sample containing 200 p.p.m. of inorganic carbon, for example, substantially with no loss of chloroform, which is a purgeable organic carbon component, and with small loss of about 6% of ethyl acetate.

Although the present invention has been described and illustrated in detail, it is clearly understood that the same is by way of illustration and example only and is not to be taken by way of limitation, the spirit and scope of the present invention being limited only by the terms of the appended claims.

The features disclosed in the foregoing description, in the claims and/or in the accompanying drawings may, both, separately and in any combination thereof, be material for realising the invention in diverse forms thereof.

What is claimed is:

1. A total organic carbon measuring apparatus, comprising:

a source of sample solution;

a first sample preparing part for acidifying said sample solution to prepare an acidified sample solution to not more than pH 4, said first sample preparing part in fluid connection with said source of sample solution;

a second sample preparing part for alkalifying said sample solution to prepare an alkalified sample solution of at least pH 9, said second sample preparing part in fluid connection with said source of sample solution;

an inorganic carbon removing part including a first chamber in fluid communication with said first sample preparing part for containing said acidified sample solution and a second chamber in fluid communication with said second sample preparing part for containing said alkalified sample solution, said inorganic carbon removing part further including a carbonic acid gas permeable material film separating said first chamber and said second chamber to allow inorganic carbon contained in said acidified sample solution to move toward said alkalified sample solution and through said carbonic acid gas permeable material film while preventing loss of purgeable organic carbon components from the acidified sample solution since the acidified sample solution and alkalified sample solution on opposite sides of the carbonic acid gas permeable material film have the same concentration of purgeable organic carbon components; and a detecting part connected to said inorganic carbon removing part for receiving said acidified sample solution from which inorganic carbon has been removed by said inorganic carbon removing part for detecting total carbon contained in said acidified sample solution.

2. A total organic measuring apparatus in accordance with claim 1, wherein said carbonic acid gas permeable material film employed in said inorganic carbon removing part is prepared from a film having continuous pores and selected from the group consisting of a polytetrafluoroethylene film, a silicone rubber film, a cellulose acetate film, a polyethylene film, and a composite film thereof.

3. A total organic carbon measuring apparatus in accordance with claim 1, wherein said inorganic carbon removing part comprises a double tube structure formed by an inner tube made of a carbonic acid gas permeable material having a sample inlet and a sample outlet on both ends thereof, and an outer tube surrounding said inner tube with a clearance provided between said inner tube and said outer tube, said outer tube having a sample inlet and a sample outlet on opposite ends thereof, said first sample preparing part having a first overflow sample container supplied with sample solution from said sample solution source from a bottom portion thereof for preparing an acidified sample solution in said first sample container with addition of an inorganic acid solution, said second sample preparing part having a second overflow sample container supplied with sample solution from said sample solution source from a bottom portion thereof for preparing an alkalified sample solution in said second sample container with addition of an alkali solution, and said total organic carbon measuring apparatus further comprises a sample injector provided between said first and second sample preparing parts and said inorganic carbon removing part for supplying a prescribed amount of said acidified sample solution prepared in said first sample preparing part into said sample inlet of said inner tube or said outer tube of said inorganic carbon removing part while supplying said alkalified sample solution prepared in said second sample preparing part into said sample inlet of said outer tube or said inner tube of said inorganic carbon removing part.

4. A total organic carbon measuring apparatus in accordance with claim 1, wherein said inorganic carbon removing part comprises a double tube structure formed by an inner tube made of a carbonic acid gas permeable material having a sample inlet and a sample outlet on opposite ends thereof, and an outer tube surrounding said inner tube with a clearance provided between said inner tube and said outer tube, said outer tube having a sample inlet and a sample outlet on opposite ends thereof;

said first sample preparing part having a first overflow sample container supplied with sample solution from said source of sample solution from a bottom portion thereof for preparing an acidified sample solution in said first sample container with addition of an inorganic acid solution, said second sample preparing part having a second overflow sample container supplied with sample solution from said source of sample solution from a bottom portion thereof for preparing an alkalified sample solution in said second sample container with addition of an alkali solution, said total organic carbon measuring apparatus further comprises a sample injector provided between said first sample preparing part and said inorganic carbon removing part for supplying a prescribed amount of said acidified sample solution prepared in said first sample preparing part into said sample inlet of said inner tube or said outer tube of said inorganic carbon removing part, and a pump for supplying said alkalified sample solution through a supply passageway for continuously supplying said alkalified sample solution prepared in said second sample preparing part into said sample inlet of said outer tube or said inner tube of said inorganic carbon removing part.

5. A total organic carbon measuring apparatus in accordance with claim 1, wherein said first and second sample preparing parts comprise an overflow sample container vertically divided by a carbonic acid gas permeable material film into two regions having sample supply ports in bottom portions thereof to be supplied with sample solution supplied from said source of sample solution so that inorganic acid solution can be added to sample solution contained in one of said regions and alkali solution can be added to sample solution contained in said other region, said overflow sample container also functioning as said inorganic carbon removing part and being provided with a sample injector for supplying a prescribed amount of acidified said sample solution from said sample container to said detecting part.

6. A total organic carbon measuring apparatus in accordance with claim 1, wherein said inorganic carbon removing part comprises a double tube structure formed by an inner tube made of a carbonic acid gas permeable material having a sample inlet and a sample outlet on opposite ends thereof, and an outer tube surrounding said inner tube with a clearance provided between said inner tube and said outer tube, said outer tube having a sample inlet and a sample outlet on opposite ends thereof, and said first sample preparing part comprising a first pump and first passageway for supplying sample solution from said source of sample solution and inorganic acid solution to said sample inlet of said inner tube or said outer tube of said inorganic carbon removing part, said second sample preparing part comprising a second pump and a second passageway for supplying sample solution from said source of sample solution and alkali solution to said sample inlet of said outer tube or said inner tube of said inorganic carbon removing part.

7. A total organic carbon measuring apparatus in accordance with claim 1, wherein said detecting part includes an oxidation reaction part being filled up with an oxidation catalyst and a carbon dioxide detecting part being supplied with a sample gas generated in said oxidation reaction part.

\* \* \* \* \*